United States Patent
Haam et al.

(10) Patent No.: US 11,535,901 B2
(45) Date of Patent: Dec. 27, 2022

(54) PROBE FOR DETECTING AND TREATING VIRUS

(71) Applicants: Yonsei University Industry Foundation (Yonsei UIF), Seoul (KR); Korea University Research and Business Foundation, Sejong Campus, Sejong-si (KR)

(72) Inventors: Seung Joo Haam, Seoul (KR); Hyun Ouk Kim, Seoul (KR); Byung Hoon Kang, Seoul (KR); Seung Min Han, Seoul (KR); Ji Sun Ki, Seoul (KR); Dae Sub Song, Daejeon (KR); Woon Sung Na, Chungcheongbuk-do (KR); Min Joo Yeom, Gyeonggi-do (KR)

(73) Assignees: Yonsei University Industry Foundation (Yonsei UIF), Seoul (KR); Korea University Research and Business Foundation, Sejong Campus, Sejong-si (KR)

( * ) Notice: Subject to any disclaimer, the term of this patent is extended or adjusted under 35 U.S.C. 154(b) by 222 days.

(21) Appl. No.: 16/142,073

(22) Filed: Sep. 26, 2018

(65) Prior Publication Data
US 2019/0093180 A1 Mar. 28, 2019

(30) Foreign Application Priority Data
Sep. 26, 2017 (KR) ......................... 10-2017-0124200

(51) Int. Cl.
*C12Q 1/6876* (2018.01)
*C12Q 1/6818* (2018.01)
*C12Q 1/70* (2006.01)

(52) U.S. Cl.
CPC ........... *C12Q 1/701* (2013.01); *C12Q 1/6818* (2013.01); *C12Q 1/6876* (2013.01); *C12Q 1/70* (2013.01)

(58) Field of Classification Search
CPC .............................. C12Q 1/701; C12Q 1/6818
See application file for complete search history.

(56) References Cited

FOREIGN PATENT DOCUMENTS

CN 103834747 A * 6/2014

OTHER PUBLICATIONS

Doria, Noble Metal Nanoparticles for Biosensing Applications, Sensors, 12, pp. 1657-1687, 2012. (Year: 2012).*
Wang, Molecular Engineering of DNA; Molecular Beacons, Angew Chem Int Ed Engl, 48(5): 856-870, 2009. (Year: 2009).*
Yadavalli, Role of metal and metal oxide nanoparticles as diagnostic and therapeutic tools for highly prevalent viral infections, Nanomedicine: NBM, 13:219-220, Jan. 2017. (Year: 2017).*
Zheng, Rationally Designed Molecular Beacons for Bioanalytical and Biomedical Applications, Chem Soc Rev, 44(10): 3036-3055, 2015. (Year: 2015).*
Mo, A nanogold-quenched fluorescence duplex probe for homogeneous DNA detection based on strand displacement, Anal. Bioanal. Chem., 389: 493-497, 2007. (Year: 2007).*
Li, A new class of homogeneous nucleic acid probes based on specific displacement hybridization, Nucleic Acid Research, 30(2): 1-9, 2002. (Year: 2002).*
Zhang et al. "DNA-Templated Silver Nanoclusters for Multiplexed Fluorescent DNA Detection", Small, 11(12): 1385-1389, Published Online Dec. 10, 2014.

* cited by examiner

*Primary Examiner* — Samuel C Woolwine
*Assistant Examiner* — Carolyn L Greene

(57) ABSTRACT

Provided herein are a probe capable of simultaneously detecting a virus and treating virus-infected cells, a composition for detecting a virus, which comprises the probe, a composition for treating a virus, which comprises the probe, and a method of detecting a virus or treating a viral infection by using the same. According to the present disclosure, it is possible to simultaneously perform diagnosis by virus detection and treatment of virus-infected cells, and in particular, diagnosis and treatment may be simultaneously performed on various types of viruses by varying the type of molecular beacon, and thus may be usefully applied to virus diagnosis and treatment fields, which require rapid diagnosis and treatment, and the spread of viral infections may be effectively prevented. In addition, the probe of the present disclosure has excellent stability and excellent detection sensitivity, and thus enables the detection of even a very low amount of a target at the pmole level.

12 Claims, 6 Drawing Sheets

Specification includes a Sequence Listing.

[FIG. 1A]
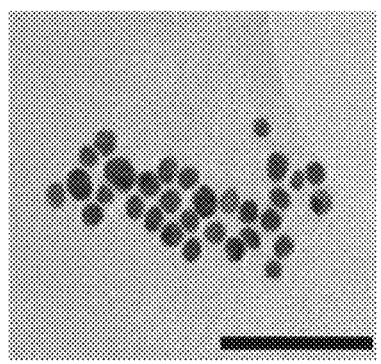
[FIG. 1B]
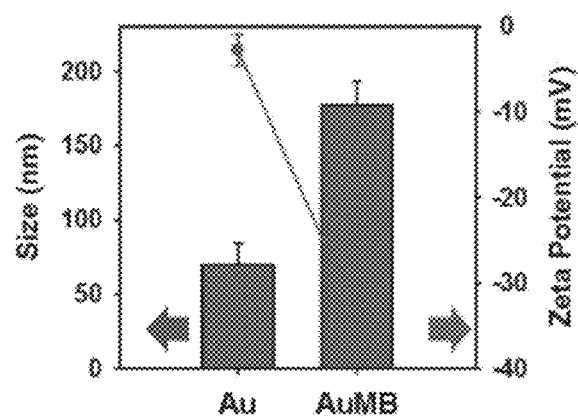

[FIG. 1C]
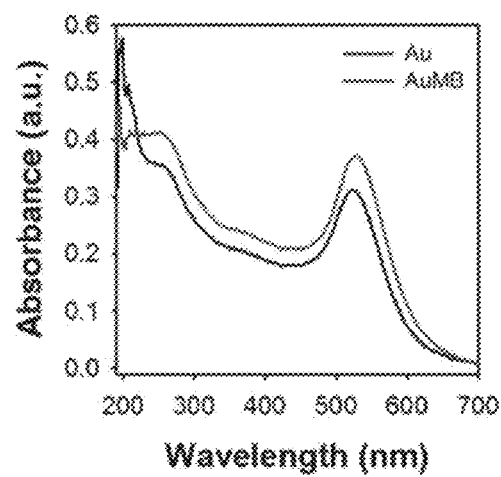
[FIG. 1D]
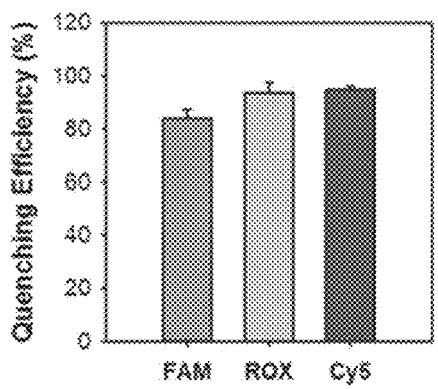

[FIG. 2A]
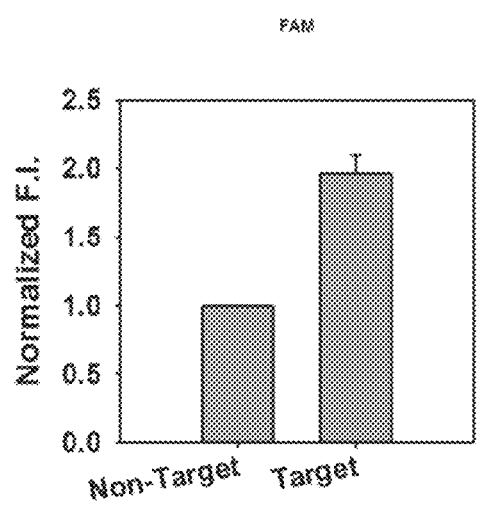
[FIG. 2B]
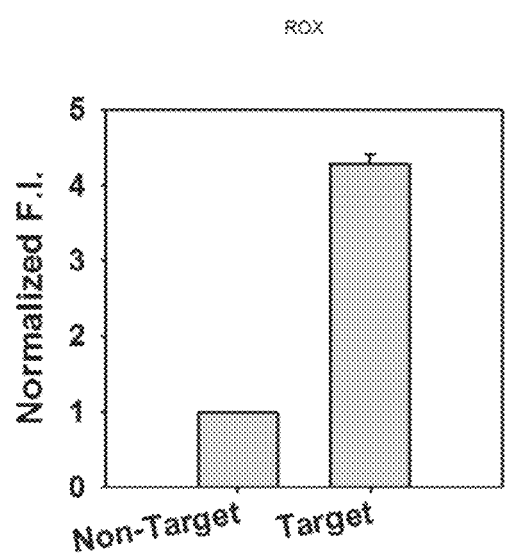

[FIG. 2C]
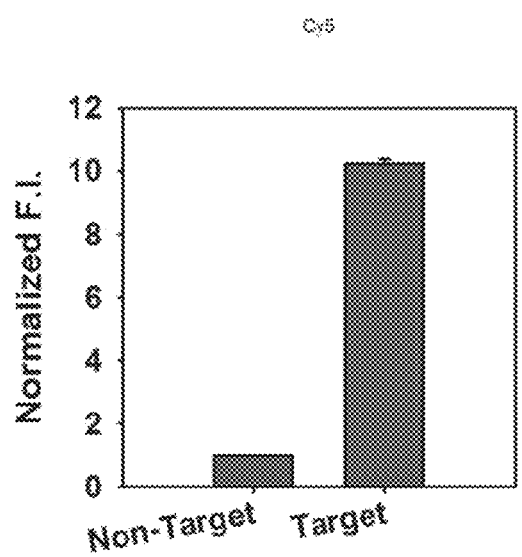
[FIG. 3A]
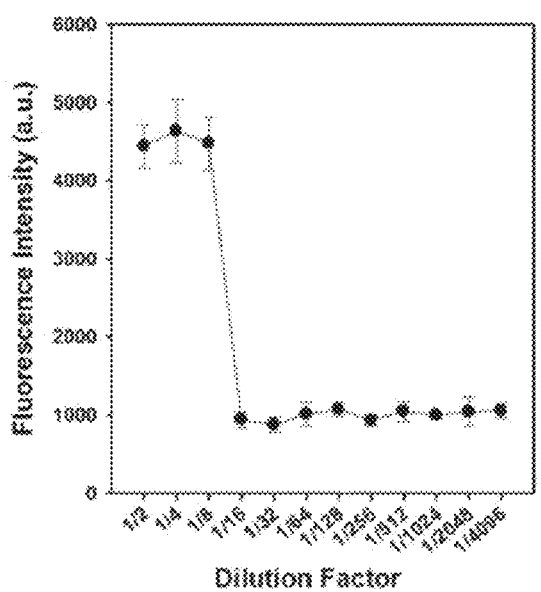

[FIG. 3B]
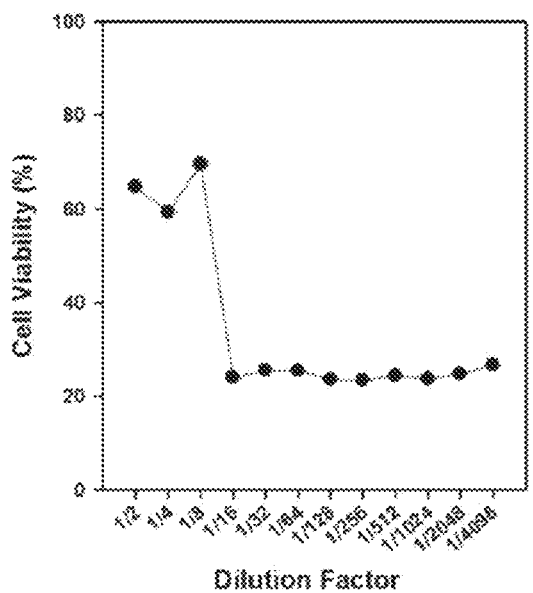
[FIG. 4A]
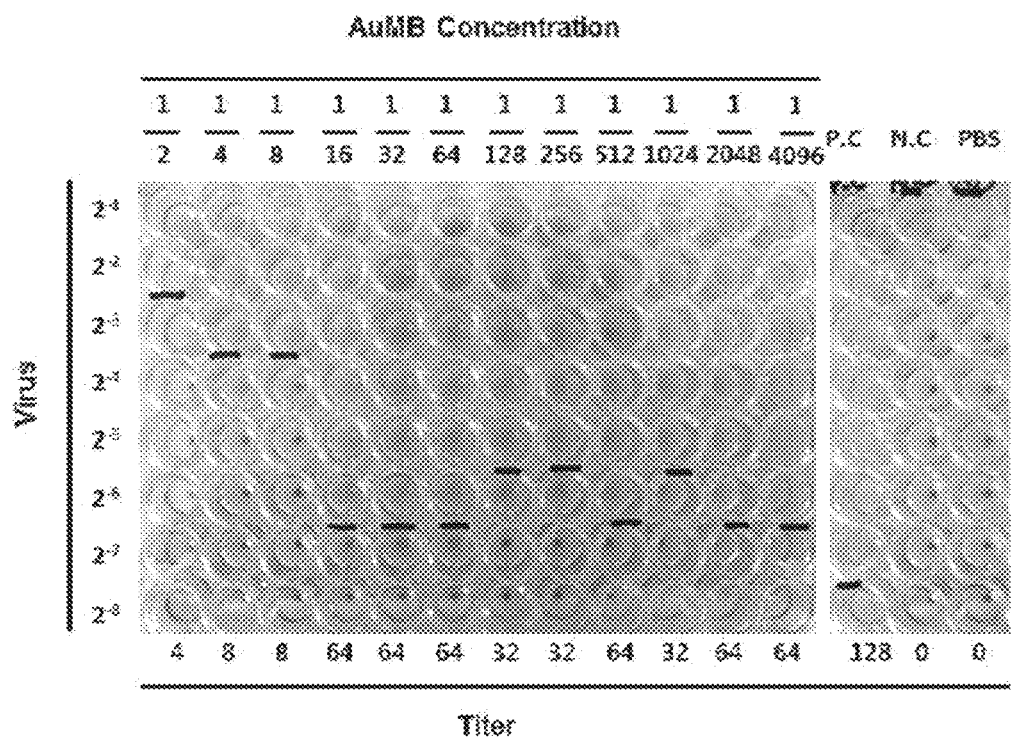

[FIG. 4B]
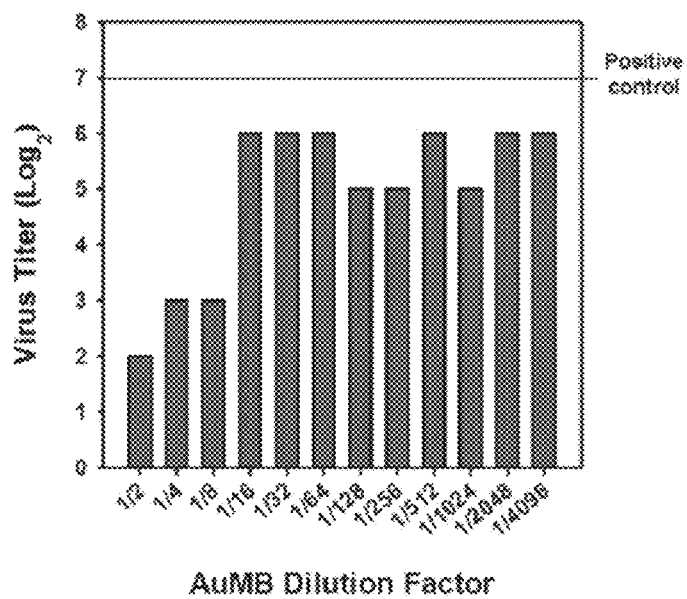
[FIG. 5]
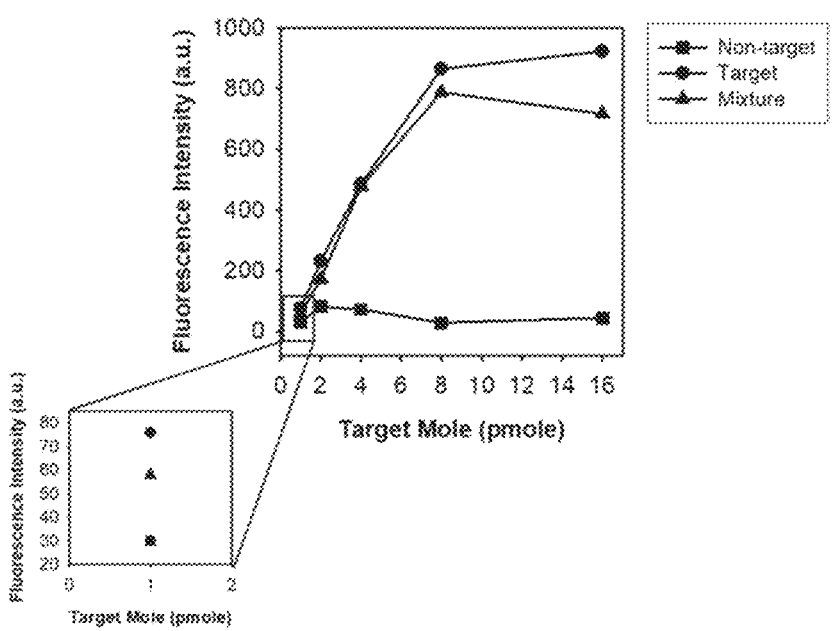

SEQUENCE LISTING

```
<160> NUMBER OF SEQ ID NOS: 40

<210> SEQ ID NO 1
<211> LENGTH: 24
<212> TYPE: DNA
<213> ORGANISM: Influenza virus
<400> SEQUENCE: 1
tctattcaat ctagaggcct attt                                              24

<210> SEQ ID NO 2
<211> LENGTH: 23
<212> TYPE: DNA
<213> ORGANISM: Influenza virus
<400> SEQUENCE: 2
agaggcaaac cagaggcctg ttc                                               23

<210> SEQ ID NO 3
<211> LENGTH: 24
<212> TYPE: DNA
<213> ORGANISM: Influenza virus
<400> SEQUENCE: 3
gctgcatcag gtagagggct attt                                              24

<210> SEQ ID NO 4
<211> LENGTH: 32
<212> TYPE: DNA
<213> ORGANISM: Artificial
<220> FEATURE:
<223> OTHER INFORMATION: molecular beacon to H1N1 virus
<220> FEATURE:
<221> NAME/KEY: misc_feature
<222> LOCATION: (1)..(11)
<223> OTHER INFORMATION: n is a, c, g, or t
<400> SEQUENCE: 4
nnnnnnnnnn ntaggcctct agattgaata ga                                     32

<210> SEQ ID NO 5
<211> LENGTH: 18
<212> TYPE: DNA
<213> ORGANISM: Artificial
<220> FEATURE:
<223> OTHER INFORMATION: molecular beacon to H1N1 virus
<220> FEATURE:
<221> NAME/KEY: misc_feature
<222> LOCATION: (1)..(9)
<223> OTHER INFORMATION: n is a, c, g, or t
<400> SEQUENCE: 5
nnnnnnnnna tccggaga                                                     18

<210> SEQ ID NO 6

-continued

<211> LENGTH: 32
<212> TYPE: DNA
<213> ORGANISM: Artificial
<220> FEATURE:
<223> OTHER INFORMATION: molecular beacon to H3N2 virus
<220> FEATURE:
<221> NAME/KEY: misc_feature
<222> LOCATION: (1)..(11)
<223> OTHER INFORMATION: n is a, c, g, or t

<400> SEQUENCE: 6
nnnnnnnnnn nacaggcctc tggtttgcct ct 32

<210> SEQ ID NO 7
<211> LENGTH: 18
<212> TYPE: DNA
<213> ORGANISM: Artificial
<220> FEATURE:
<223> OTHER INFORMATION: molecuar beacon to H3N2
<220> FEATURE:
<221> NAME/KEY: misc_feature
<222> LOCATION: (1)..(9)
<223> OTHER INFORMATION: n is a, c, g, or t

<400> SEQUENCE: 7
nnnnnnnnnt gtccggag 18

<210> SEQ ID NO 8
<211> LENGTH: 32
<212> TYPE: DNA
<213> ORGANISM: Artificial
<220> FEATURE:
<223> OTHER INFORMATION: molecuar beacon to H9N2
<220> FEATURE:
<221> NAME/KEY: misc_feature
<222> LOCATION: (1)..(11)
<223> OTHER INFORMATION: n is a, c, g, or t

<400> SEQUENCE: 8
nnnnnnnnnn ntagccctct acctgatgca gc 32

<210> SEQ ID NO 9
<211> LENGTH: 18
<212> TYPE: DNA
<213> ORGANISM: Artificial
<220> FEATURE:
<223> OTHER INFORMATION: molecuar beacon to H9N2
<220> FEATURE:
<221> NAME/KEY: misc_feature
<222> LOCATION: (1)..(9)
<223> OTHER INFORMATION: n is a, c, g, or t

<400> SEQUENCE: 9
nnnnnnnnna tcgggaga 18

<210> SEQ ID NO 10
<211> LENGTH: 32
<212> TYPE: DNA
<213> ORGANISM: Artificial
<220> FEATURE:
<223> OTHER INFORMATION: molecular beacon to H1N1 virus

<400> SEQUENCE: 10
gggggaaatt ttaggcctct agattgaata ga 32

<210> SEQ ID NO 11
<211> LENGTH: 18
<212> TYPE: DNA
<213> ORGANISM: Artificial

```
<220> FEATURE:
<223> OTHER INFORMATION: molecular beacon to H1N1 virus

<400> SEQUENCE: 11
ccctttaaaa tccggaga                                                      18

<210> SEQ ID NO 12
<211> LENGTH: 32
<212> TYPE: DNA
<213> ORGANISM: Artificial
<220> FEATURE:
<223> OTHER INFORMATION: molecular beacon to H1N1 virus

<400> SEQUENCE: 12
gggggcaatt ttaggcctct agattgaata ga                                      32

<210> SEQ ID NO 13
<211> LENGTH: 18
<212> TYPE: DNA
<213> ORGANISM: Artificial
<220> FEATURE:
<223> OTHER INFORMATION: molecular beacon to H1N1 virus

<400> SEQUENCE: 13
cccgttaaaa tccggaga                                                      18

<210> SEQ ID NO 14
<211> LENGTH: 32
<212> TYPE: DNA
<213> ORGANISM: Artificial
<220> FEATURE:
<223> OTHER INFORMATION: molecular beacon to H1N1 virus

<400> SEQUENCE: 14
gggggccatt ttaggcctct agattgaata ga                                      32

<210> SEQ ID NO 15
<211> LENGTH: 18
<212> TYPE: DNA
<213> ORGANISM: Artificial
<220> FEATURE:
<223> OTHER INFORMATION: molecular beacon to H1N1 virus

<400> SEQUENCE: 15
cccggtaaaa tccggaga                                                      18

<210> SEQ ID NO 16
<211> LENGTH: 32
<212> TYPE: DNA
<213> ORGANISM: Artificial
<220> FEATURE:
<223> OTHER INFORMATION: molecular beacon to H1N1 virus

<400> SEQUENCE: 16
gggggccctt ttaggcctct agattgaata ga                                      32

<210> SEQ ID NO 17
<211> LENGTH: 18
<212> TYPE: DNA
<213> ORGANISM: Artificial
<220> FEATURE:
<223> OTHER INFORMATION: molecular beacon to H1N1 virus

<400> SEQUENCE: 17
cccgggaaaa tccggaga                                                      18
```

-continued

<210> SEQ ID NO 18
<211> LENGTH: 32
<212> TYPE: DNA
<213> ORGANISM: Artificial
<220> FEATURE:
<223> OTHER INFORMATION: molecular beacon to H1N1 virus

<400> SEQUENCE: 18
gggggcccgt ttaggcctct agattgaata ga 32

<210> SEQ ID NO 19
<211> LENGTH: 18
<212> TYPE: DNA
<213> ORGANISM: Artificial
<220> FEATURE:
<223> OTHER INFORMATION: molecular beacon to H1N1 virus

<400> SEQUENCE: 19
cccgggcaaa tccggaga 18

<210> SEQ ID NO 20
<211> LENGTH: 32
<212> TYPE: DNA
<213> ORGANISM: Artificial
<220> FEATURE:
<223> OTHER INFORMATION: molecular beacon to H1N1 virus

<400> SEQUENCE: 20
gggggcccgg ttaggcctct agattgaata ga 32

<210> SEQ ID NO 21
<211> LENGTH: 18
<212> TYPE: DNA
<213> ORGANISM: Artificial
<220> FEATURE:
<223> OTHER INFORMATION: molecular beacon to H1N1 virus

<400> SEQUENCE: 21
cccgggccaa tccggaga 18

<210> SEQ ID NO 22
<211> LENGTH: 32
<212> TYPE: DNA
<213> ORGANISM: Artificial
<220> FEATURE:
<223> OTHER INFORMATION: molecular beacon to H1N1 virus

<400> SEQUENCE: 22
gggggcccgg gtaggcctct agattgaata ga 32

<210> SEQ ID NO 23
<211> LENGTH: 18
<212> TYPE: DNA
<213> ORGANISM: Artificial
<220> FEATURE:
<223> OTHER INFORMATION: molecular beacon to H1N1 virus

<400> SEQUENCE: 23
cccgggccca tccggaga 18

<210> SEQ ID NO 24
<211> LENGTH: 32
<212> TYPE: DNA
<213> ORGANISM: Artificial
<220> FEATURE:
<223> OTHER INFORMATION: molecular beacon to H1N1 virus

<400> SEQUENCE: 24
gggggcactt ttaggcctct agattgaata ga 32

<210> SEQ ID NO 25
<211> LENGTH: 18
<212> TYPE: DNA
<213> ORGANISM: Artificial
<220> FEATURE:
<223> OTHER INFORMATION: molecular beacon to H1N1 virus

<400> SEQUENCE: 25
cccgtgaaaa tccggaga 18

<210> SEQ ID NO 26
<211> LENGTH: 32
<212> TYPE: DNA
<213> ORGANISM: Artificial
<220> FEATURE:
<223> OTHER INFORMATION: molecular beacon to H3N2 virus

<400> SEQUENCE: 26
gggggcactt tacaggcctc tggtttgcct ct 32

<210> SEQ ID NO 27
<211> LENGTH: 18
<212> TYPE: DNA
<213> ORGANISM: Artificial
<220> FEATURE:
<223> OTHER INFORMATION: molecular beacon to H3N2 virus

<400> SEQUENCE: 27
cccgtgaaat gtccggag 18

<210> SEQ ID NO 28
<211> LENGTH: 32
<212> TYPE: DNA
<213> ORGANISM: Artificial
<220> FEATURE:
<223> OTHER INFORMATION: molecular beacon to H9N2 virus

<400> SEQUENCE: 28
gggggcactt ttagccctct acctgatgca gc 32

<210> SEQ ID NO 29
<211> LENGTH: 18
<212> TYPE: DNA
<213> ORGANISM: Artificial
<220> FEATURE:
<223> OTHER INFORMATION: molecular beacon to H9N2 virus

<400> SEQUENCE: 29
cccgtgaaaa tcgggaga 18

<210> SEQ ID NO 30
<211> LENGTH: 32
<212> TYPE: DNA
<213> ORGANISM: Artificial
<220> FEATURE:
<223> OTHER INFORMATION: molecular beacon to H1N1 virus

<400> SEQUENCE: 30
tttttaaatt ttaggcctct agattgaata ga 32

<210> SEQ ID NO 31

```
<211> LENGTH: 18
<212> TYPE: DNA
<213> ORGANISM: Artificial
<220> FEATURE:
<223> OTHER INFORMATION: molecular beacon to H1N1 virus

<400> SEQUENCE: 31
aaatttaaaa tccggaga                                                 18

<210> SEQ ID NO 32
<211> LENGTH: 32
<212> TYPE: DNA
<213> ORG

```
caatttaaaa tccggaga                                                     18

<210> SEQ ID NO 38
<211> LENGTH: 32
<212> TYPE: DNA
<213> ORGANISM: Artificial
<220> FEATURE:
<223> OTHER INFORMATION: molecular beacon to H1N1 virus

<400> SEQUENCE: 38
ggggtaaatt ttaggcctct agattgaata ga                                     32

<210> SEQ ID NO 39
<211> LENGTH: 18
<212> TYPE: DNA
<213> ORGANISM: Artificial
<220> FEATURE:
<223> OTHER INFORMATION: molecular beacon to H1N1 virus

<400> SEQUENCE: 39
ccatttaaaa tccggaga                                                     18

<210> SEQ ID NO 40
<211> LENGTH: 15
<212> TYPE: DNA
<213> ORGANISM: Artificial
<220> FEATURE:
<223> OTHER INFORMATION: scramble sequence

<400> SEQUENCE: 40
gtacttatta ggcgg                                                        15
```

PROBE FOR DETECTING AND TREATING VIRUS

RELATED APPLICATION

This application claims priority to and the benefit of Korean Patent Application No. 2017-0124200, filed on Sep. 26, 2017, the disclosure of which is incorporated herein by reference in its entirety.

SEQUENCE LISTING STATEMENT

The ASCII file, entitled 75513SequenceListing.txt, created on Sep. 26, 2017, comprising 8,249 bytes, submitted concurrently with the filing of this application is incorporated herein by reference. The sequence listing submitted herewith is identical to the sequence listing forming part of the international application.

FIELD AND BACKGROUND OF THE INVENTION

1. Field

The present disclosure relates to a probe capable of simultaneously performing the detection of a virus and the treatment of virus-infected cells, a composition for detecting a virus, which comprises the probe, a composition for treating a virus, which comprises the probe, and a method of detecting a virus or treating a viral infection by using the same.

2. Discussion of Related Art

Although antiviral agents are required to treat and control viral diseases, antiviral agents currently sold on the market are very limited as compared to antibiotics. As drugs targeting influenza, oseltamivir and zanamivir, which are neuraminidase (NA) inhibitors, and amantadine and rimantadine, which are M2 protein inhibitors, have been developed. In particular, NA inhibitors belong to exemplary drugs developed by structure-based drug design, and an NA inhibitor designed and discovered as a substrate inhibitor using the tertiary structure of influenza NA, which was discovered in the early 1990s, is oseltamivir.

However, in the case of viruses, the occurrence of mutation is so rapid that drug-resistant viruses against NA inhibitors and M2 inhibitors have already been seriously generated, and there are currently many limitations in treating viruses due to severe side effects of the M2 inhibitors.

In addition, it is difficult to develop fundamental vaccines due to the occurrence of various mutations of viruses, and since viruses spread so fast, it is most important to prevent the spread of diseases through early diagnosis and treatment. As methods of detecting viruses, immunological detection methods such as enzyme-linked immunosorbent assay (ELISA), enzyme immunoassay (EIA), immunofluorescence assay (IFA), and the like, and RNA detection by real-time polymerase chain reaction (RT-PCR) are known. However, when these methods are used, an excess amount of time is required to detect and diagnose viruses, expensive testing costs are required, or specificity and sensitivity are reduced due to a non-specific reaction, and thus there are still many difficulties in the early detection of viruses.

Therefore, there is still a need to research a method of detecting and treating a virus to overcome existing limitations in the diagnosis and treatment of viruses and address existing difficulties.

SUMMARY OF THE INVENTION

To overcome the existing limitations in diagnosis and treatment of viruses, studies continued to be conducted on agents for treating and detecting viruses that do not target NA and M2 of existing viruses, but target other proteins, and consequently, a probe capable of detecting a virus without resistance problems by targeting a gene present in the genome of the virus and treating a viral infection by suppressing the proliferation of the virus genome was developed and an effect thereof was identified, thus completing the present disclosure.

According to an aspect of an embodiment, there is provided a probe for detecting and/or treating a virus, comprising: metal particles; and a molecular beacon comprising an anti-target nucleic acid molecule and an oligo nucleic acid molecule, wherein the anti-target nucleic acid molecule binds to surfaces of the metal particles and comprises a non-target site and a target-specific binding site; the oligo nucleic acid molecule comprises a non-target site, an anti-target nucleic acid molecule-complementary binding site and a fluorescent material; the a non-target site of anti-target nucleic acid molecule and a non-target site of oligo nucleic acid molecule comprise a ratio of cytosine (C)/guanine (G) in 50% or more, respectively; and one or more molecular beacons are bound to the metal particles.

According to an aspect of another embodiment, there is provided a composition for detecting a virus, which comprises the probe.

According to an aspect of another embodiment, there is provided a composition for treating a viral infection, which comprises the probe.

According to an aspect of another embodiment, there is provided a method of detecting a virus, which comprises contacting a sample obtained from a subject with the probe according to claim 1; and measuring a change in fluorescence of the sample contacted with the probe.

BRIEF DESCRIPTION OF THE SEVERAL VIEWS OF THE DRAWINGS

The above and other objects, features and advantages of the present disclosure will become more apparent to those of ordinary skill in the art by describing in detail exemplary embodiments thereof with reference to the accompanying drawings, in which:

FIGS. 1A, 1B, 1C, and 1D illustrate verification results of morphological and physical characteristics of a probe of the present disclosure;

FIGS. 2A, 2B, and 2C illustrate verification results of fluorescence/quenching characteristics of a probe of the present disclosure;

FIGS. 3A and 3B are graphs showing identification results of an effect of a probe of the present disclosure on detecting and treating a virus in vitro;

FIGS. 4A and 4B illustrate hemagglutination (HA) assay identification results of an effect of a probe of the present disclosure on detecting and treating a virus in vitro; and FIG. 5 illustrates results of verifying the detectability of probes of the present disclosure according to the amount of a detection target, wherein a horizontal axis of the graph denotes the amount (pmole) of a target, which is an object to be detected by the probe of the present disclosure, and a vertical axis of the graph denotes a value of fluorescence emitted from the probe: "Non-target" denotes a change in fluorescence according to the amount of non-targets in samples; "Target" denotes a change in fluorescence according to the amount of targets in samples; and "Mixture" denotes a change in fluorescence according to the amount of the targets and the non-targets in samples.

DESCRIPTION OF SPECIFIC EMBODIMENTS OF THE INVENTION

Exemplary embodiments of the present disclosure will be described in detail below with reference to the accompanying drawings. While the present disclosure is shown and described in connection with exemplary embodiments thereof, it will be apparent to those skilled in the art that various modifications can be made without departing from the spirit and scope of the disclosure.

The present disclosure relates to a probe for detecting or treating a virus, which comprises: metal particles; and a molecular beacon comprising an anti-target nucleic acid molecule and an oligo nucleic acid molecule.

As used herein, the term "probe" refers to a substance for detecting a specific material, and in particular, refers to a substance for detecting a target virus. The probe of the present disclosure may comprise metal particles and a molecular beacon bound to the metal particles. The probe diagnoses the presence of a virus by detecting a target virus by the molecular beacon and, at the same time, has a therapeutic effect of inhibiting the proliferation of the virus by binding thereto by the molecular beacon. In addition, the probe may comprise two or more molecular beacons, and thus enables the simultaneous detection of various types of viruses.

As used herein, the term "target" refers to an object to be detected or diagnosed by the probe, and the target may particularly be a virus. More particularly, the target comprises a gene encoding a protein or a fragment of the protein of the virus and genetic materials as long as it is capable of complementarily binding to the molecular beacon of the present disclosure.

The virus may be, for example, an influenza virus. Regarding the influenza virus, there are various subtypes comprising H1N1, H2N2, H3N2, H5N1, H7N7, and H9N2, and the probe of the present disclosure has been devised to be applicable to various subtypes of viruses when designing the anti-target nucleic acid molecule having a virus-binding site, and thus the type of virus is not limited.

In one embodiment of the present disclosure, diagnostic and therapeutic effects of the probe of the present disclosure on H1N1, H3N2, and H9N2 were verified.

As used herein, the term "molecular beacon" refers to a substance enabling identification of the presence of a specific nucleic acid and a substance capable of specifically binding to a genetic material (RNA or the like) encoding a protein of a virus to enable identification of the presence of the virus. The molecular beacon comprises an anti-target nucleic acid molecule comprising a target-specific binding site capable of specifically binding to a target and an oligo nucleic acid molecule comprising an anti-target nucleic acid molecule-complementary binding site and a fluorescent material. The molecular beacon of the present disclosure is bound to the metal particles before coming into contact with a target and maintains a quenching state, and when being in contact with the target, the anti-target nucleic acid molecule of the molecular beacon binds to the target, and the presence of the target may be detected using a method of measuring fluorescence emitted by separation of the oligo nucleic acid molecule comprising a fluorescent material from the molecular beacon.

The molecular beacon may comprise an anti-target nucleic acid molecule and an oligo nucleic acid molecule.

The anti-target nucleic acid molecule comprises a non-target site and a target-specific binding site.

The anti-target nucleic acid molecule of the molecular beacon binds to surfaces of the metal particles and comprises a non-target site and a target-specific binding; the oligo nucleic acid molecule comprises a non-target site, an anti-target nucleic acid molecule-complementary binding site and a fluorescent material; the a non-target site of anti-target nucleic acid molecule and a non-target site of oligo nucleic acid molecule comprise a ratio of cytosine (C)/guanine (G) in 50% or more, respectively; and one or more molecular beacons are bound to the metal particles.

The term "target-specific binding site" as used herein refers to a nucleic acid sequence comprising a sequence complementary to a target virus or a fragment thereof, and in particular, the target-specific binding site may comprise a sequence complementarily binding to a sequence of a genetic material encoding a protein of the target virus or a fragment thereof, or may consist of the complementary nucleic acid sequence. As used herein, the complementary nucleic acid sequence refers to a base sequence capable of forming a double-stranded structure through formation of base pairs (adenine (A)-thymine (T) and guanine (G)-cytosine (C)) with a nucleic acid sequence of the target.

The genetic material or fragment thereof of the target virus to which the target-specific binding site of the present disclosure complementarily binds may be designed according to a complementary sequence based on sequences known in the art on which nucleic acid sequence analysis has been completed, and thus may be clearly specified without being limited to the nucleic acid sequence.

For example, the target-specific binding site may have a sequence with at least 90% homology, preferably at least 95% homology to a portion of RNA of a virus or a fragment thereof. The length of a site capable of binding to the target virus (target-specific binding site) may be appropriately adjusted according to a target virus or a binding site of the virus, and is not necessarily limited to a particular length. For example, when the target is a stem region of an influenza virus, the target-specific binding site may consist of 2 to 40 consecutive nucleic acid molecules complementary to a sequence of the stem region of the virus, but may be shorter or longer than the above case, in the case of different virus subtypes or a region capable of binding to RNA of another site of a virus.

In one embodiment of the present disclosure, the anti-target nucleic acid molecule was devised such that the target-specific binding site complementarily binds to RNA encoding a stem region of the HA protein in each subtype of an influenza virus, and it was confirmed that each subtype of influenza virus was detectable using this. More particularly, the target-specific binding site of the present disclosure may comprise a nucleic acid sequence complementary to any one nucleic acid sequence selected from the group consisting of SEQ ID NOS: 1 to 3. In another embodiment, the target-specific binding site of the present disclosure may comprise a nucleic acid molecule comprising 2 to 24 nucleotides complementarily binding to any one nucleic acid sequence selected from the group consisting of SEQ ID NOS: 1 to 3, or may be a nucleic acid molecule consisting of the 2 to 24 nucleotides.

The term "non-target site" as used herein refers to a nucleic acid sequence that does not complementarily bind to a target such as a virus or a fragment thereof, and comprises all nucleic acid sequences that may be comprised, in addition to the nucleic acid sequence constituting the target-specific binding site complementarily binding to a virus, which is a target to be detected. The non-target site may comprise or consist of 4 to 20 short nucleic acid sequences consisting of bases selected from A, T, G, and C. In the present disclosure, the non-target site comprises a nucleic acid sequence that does not complementarily bind to a target virus or a fragment thereof, but complementarily binds to the non-target site of the oligo nucleic acid molecule of the present disclosure.

It is significant that the molecular beacon of the present disclosure comprises the non-target site, in that detection performance and the like of the molecular beacon is adjustable by the type of base comprised in the non-target site, or the like, and in particular, a ratio of C/G among A, T, G, and C in the nucleic acid sequence of the non-target site may be 50% or more. In this case, the molecular beacon may exhibit enhanced stability, and thus detection of the virus target by the molecular beacon and a therapeutic effect thereof may be enhanced.

In the anti-target nucleic acid molecule of the present disclosure, an end of the non-target site may bind to an end of the target-specific binding site, and another end of the non-target site may have a linker linked thereto for binding to the metal particles. That is, an end of the anti-target nucleic acid molecule may be modified with a linker, and the anti-target nucleic acid molecule of the present disclosure may have a [linker]-[non-target site]-[target-specific binding site] structure. In a case in which the non-target site is placed close to the metal particles, a difference in luminescence emitted when the oligo nucleic acid molecule and the anti-target nucleic acid molecule are bound and are separated from each other may be controlled by adjusting the nucleic acid sequence of the non-target site, and thus it is possible to control detection sensitivity and accuracy of the target by using the probe of the present disclosure.

In one embodiment, the anti-target nucleic acid molecule may consist of a nucleic acid sequence of SEQ ID NO: 4; SEQ ID NO: 6; or SEQ ID NO: 8. In SEQ ID NO: 4; SEQ ID NO: 6; or SEQ ID NO: 8, n may be A, T, G, or C.

In addition, in SEQ ID NO: 4; SEQ ID NO: 6; or SEQ ID NO: 8, a ratio of C/G in a total number of n may be 50% or more. In this case, the probe of the present disclosure may have further enhanced effects of detecting and treating a target material. In addition, a sequence consisting of n in SEQ ID NO: 4; SEQ ID NO: 6; or SEQ ID NO: 8 complementarily binds to a sequence consisting of n in SEQ ID NO: 5; SEQ ID NO: 7; or SEQ ID NO: 9 or a segment thereof.

In addition, the anti-target nucleic acid molecule may comprise any one nucleic acid sequence selected from the group consisting of SEQ ID NOS: 10, 12, 14, 16, 18, 20, 22, 24, 26, and 28.

The anti-target nucleic acid molecule binds to surfaces of the metal particles. The molecular beacon of the present disclosure may further comprise a linker between the anti-target nucleic acid molecule and the metal particles. The linker may be a functional group used to modify surfaces of organic particles or inorganic particles comprising metal particles in the art to which the present disclosure pertains or a compound containing the same, without limitation. The functional group may be, for example, a thiol group, an amine group, or a phosphine, but the present disclosure is not limited thereto. Preferably, when the metal particles of the present disclosure are gold particles, the functional group may be a thiol group since the thiol group has high adsorption onto surfaces of gold nanoparticles. When the nucleic acid molecule and the metal particles of the present disclosure are bound to each other via a thiol group linker, adsorption thereof onto surfaces of the metal particles is excellent, and thus a larger number of molecular beacons may be bound to the metal particles.

The probe of the present disclosure may comprise one or more molecular beacons, preferably two or more molecular beacons. The two or more molecular beacons comprised in the probe may be identical to each other or different from each other, and may target the same virus or different viruses. When the probe comprises two or more molecular beacons targeting different viruses, the probe has an excellent effect in that two or more viruses may be simultaneously diagnosed and treated using the probe. In particular, when the probe of the present disclosure comprises two or more molecular beacons and each of the anti-target nucleic acid molecules of the two or more molecular beacons independently has a target-specific binding site for different viruses, the molecular beacons may bind to different viruses, thereby having diagnostic and therapeutic effects. Therefore, in this aspect, the present disclosure provides a probe for detecting and treating various types of viruses. In particular, the probe of the present disclosure is advantageous in that even when the probe comprises two or more molecular beacons that bind to respective targets, each molecular beacon has excellent stability and has no interference with the other targets, and thus very low amount of multiple targets may also be effectively detected.

The molecular beacon comprises an oligo nucleic acid molecule comprising an anti-target nucleic acid molecule-complementary binding site and a fluorescent material.

The anti-target nucleic acid molecule-complementary binding site is a site that complementarily binds to bases of the anti-target nucleic acid molecule, and may be a nucleic acid sequence (5 mer to 10 mer) consisting of 5 to 10 nucleotides.

The oligo nucleic acid molecule may further comprise a non-target site. The non-target site of the oligo nucleic acid molecule comprises all nucleic acid sequences that may be comprised, in addition to the nucleic acid sequence constituting the target-specific binding site complementarily binding to a virus to be detected. The non-target site may comprise or consist of 4 to 20 short nucleic acid sequences consisting of bases selected from A, T, G, and C. The non-target site of the oligo nucleic acid molecule may complementarily bind to a partial sequence of the non-target site of the anti-target nucleic acid molecule. In particular, the non-target site of the oligo nucleic acid molecule may comprise a nucleic acid sequence (5 mer to 10 mer) consisting of 5 to 10 nucleotides complementarily binding to the nucleic acid sequence of the non-target site of the anti-target nucleic acid molecule.

It is significant that the molecular beacon of the present disclosure comprises the non-target site, in that detection performance and the like of the molecular beacon is adjustable by the type of base comprised in the non-target site, or the like, and in particular, a ratio of C/G among A, T, G, and C in the nucleic acid sequence of the non-target site may be 50% or more. In this case, the molecular beacon may exhibit enhanced stability, and thus detection of the target virus by the molecular beacon and a therapeutic effect thereof may be enhanced.

The fluorescent material comprised in each beacon may have each independently different emission wavelengths. In this case, the presence or absence of viral infection may be detected using one probe in cells infected with two or more viruses and measurement may be performed thereon by varying only a wavelength, thereby rapidly detecting whether or not cells were infected with various types of viruses, and it is possible to perform diagnosis for various types of viruses with even a small amount of sample, and accordingly, diagnosis time may be significantly shortened as compared to the related art.

The fluorescent material bound to an end of the oligo nucleic acid molecule may be any fluorescent material that may be used in imaging in vitro or in vivo. In one embodiment, the fluorescent material may be selected from, but is not limited thereto, rhodamine or derivatives thereof, fluorescein or derivatives thereof, coumarin or derivatives thereof, acridine and derivatives thereof, pyrene and derivatives thereof, erythrosine and derivatives thereof, eosin or derivatives thereof, cyanine or derivatives thereof, and 4-acetamido-4'-isothiocyanatostilbene-2,2'-disulfonic acid. More specific examples of the fluorescent material are as follows:

rhodamine and derivatives thereof: 6-carboxy-X-rhodamine (ROX, Ex/Em: 574/602), 6-carboxyrhodamine (R6G), lysamin rhodamine B sulfonyl chloride, rhodamine (Rhod), rhodamine B, rhodamine 123, rhodamine X isothiocyanate, sulforhodamine B, sulforhodamine 101, sulfonyl chloride derivatives of sulforhodamine 101 (Texas Red, Ex/Em: 595/615), N,N,N',N'-tetramethyl-6-carboxyrhodamine (TAMRA, Ex/Em: 542/568), tetramethyl rhodamine, tetramethyl rhodamine isothiocyanate (TRITC), riboflavin, rosolic acid, terbium chelate derivatives, Alexa derivatives, Alexa-350, Alexa-488, Alexa-547, and Alexa-647 (Ex/Em: 653/669);

fluorescein and derivatives thereof: 5'-carboxyfluorescein (FAM, Ex/Em: 490/520), 5-(4,6-dichlorotriazine-2-yl)aminofluorescein (DTAF), 2',7'-dimethoxy-4',5'-dichloro-6-carboxyfluorescein (JOE, Ex/Em: 525/555), fluorescein, fluorescein isothiocyanate, QFITC (XRITC), fluorescamine, IR144, IR1446, malachite green isothiocyanate, 4-methylumbelliferone, orthocresolphthalein, nitrotyrosine, pararosaniline, phenol red, B-picoerythrin, and o-phthaldialdehyde;

coumarin and derivatives thereof: coumarin, 7-amino-4-methylcoumarin (AMC, coumarin 120), 7-amino-4-trifluoromethylcoumarin (coumarin 151), cyanosine, 4'-6-diaminidino-2-phenylindole (DAPI), 5',5''-dibromopyrogallolsulfonephthalein (Bromopyrogallol Red), 7-diethylamino-3-(4'-isothiocyanatophenyl)-4-methylcoumarin diethylenetriamine pentaacetate, 4-(4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), 4-(4'-dimethylaminophenylazo)benzoic acid (DABCYL), and 4-dimethylaminophenylazophenyl-4'-isothiocyanate (DABITC);

acridine and derivatives thereof: acridine, acridine isothiocyanate, 5-(2'-aminoethyl)aminonaphthalene-1-sulfonic acid (EDANS), 4-amino-N-[3-vinylsulfonyl]phenyl]naphthalimide-3,5-disulfonate, N-(4-anilino-1-naphthyl) maleimide, anthranylamide, and Brilliant Yellow;

pyrene and derivatives thereof: pyrene, pyrene butyrate, succinimidyl 1-pyrene butyrate, and Reactive Red 4 (Cibacron® Brilliant Red 3B-A);

erythrosine and derivatives thereof: erythrosine B, erythrosine isothiocyanate, and ethidium;

eosin and derivatives thereof: eosin and eosin isothiocyanate;

cyanine and derivatives thereof: cyanine 2 (Cy2, Ex/Em: 489/506), cyanine 3 (Cy3, Ex/Em: (512); 550/570; (615), cyanine 3B (Cy3B, Ex/Em: 558/572(620)), cyanine 3.5 (Cy3.5, Ex/Em: 581/594(640)), cyanine 5 (Cy5, Ex/Em: (625); 650/670), cyanine 5.5 (Cy5.5, 5, Ex/Em: 675/694), and cyanine 7 (Cy7, Ex/Em: 743/767); and 4-acetamido-4'-isothiocyanatostilbene-2,2'-disulfonic acid.

The oligo nucleic acid molecule may consist of a nucleic acid sequence of SEQ ID NO: 5; SEQ ID NO: 7; or SEQ ID NO: 9. In SEQ ID NO: 5; SEQ ID NO: 7; or SEQ ID NO: 9, n may be A, T, G, or C. In addition, in SEQ ID NO: 5; SEQ ID NO: 7; or SEQ ID NO: 9, a ratio of C/G in a total number of n may be 50% or more. In this case, the probe of the present disclosure may have further enhanced effects of detecting and treating a target material.

In addition, the oligo nucleic acid molecule may comprise any one nucleic acid sequence selected from the group consisting of SEQ ID NOS: 11, 13, 15, 17, 19, 21, 23, 25, 27, and 29.

The oligo nucleic acid molecule may be in a form in which a fluorescent material is bound to one end of a site capable of binding to the anti-target nucleic acid molecule (anti-target nucleic acid molecule-complementary binding site), and the fluorescent material may be located close to the metal particles. The anti-target nucleic acid molecule-complementary binding site may comprise a part of nucleic acid sequence of targets. The non-target site of the oligo nucleic acid molecule may be able to complementarily bound to the non-target site of the anti-target nucleic acid molecule. In this case, the sensitivity and stability of the molecular beacon of the present invention can be controlled by a ratio of C/G in the nucleic acid sequence of the non-target site. More preferably, the oligo nucleic acid molecule of the present disclosure may have a [fluorescent material]-[non-target site]-[anti-target nucleic acid molecule-complementary binding site] structure. In this case, the fluorescent material may be located close to the metal particles in the probe, so that a stronger extinction state can be maintained in the inactivated molecular beacon before meeting the target.

The probe of the present disclosure may be designed such that complementary binding between the anti-target nucleic acid molecule and the target is better than between the anti-target nucleic acid molecule and the oligo nucleic acid molecule. For this, the oligo nucleic acid molecule may have a smaller length of polynucleotides than that of the anti-target nucleic acid molecule. In this case, when a virus or a fragment thereof is present, the oligo nucleic acid molecule is easily separated from the anti-target nucleic acid molecule, and thus complementary binding between the anti-target nucleic acid molecule and the target may be formed more strongly, and accordingly, when a target virus is present, a fluorescence effect due to separation of the oligo nucleic acid molecule may be more satisfactorily identified.

The Tm value of the molecular beacon may vary according to ratios of C/G and A/T present in the nucleic acid sequence of the non-target site or anti-target nucleic acid molecule-complementary binding site of the present disclosure.

In the present invention, the "Tm value" means a temperature at which 50% of the nucleic acid molecules dissociated in the pair of complementarily bound nucleic acid molecules are present. Before the molecular beacon of the present disclosure meets with the target, the anti-target nucleic acid molecule and the oligo nucleic acid molecule in the molecular beacon must remain coupled, and then when the molecular beacon meets with the target the oligo nucleic acid molecule must be released from the anti-target nucleic acid molecule to form an anti-target nucleic acid molecule-target complex and to emit fluorescence. Therefore, it is very important to design respective sites of the nucleic acid molecules to have an appropriate Tm value in the molecular beacon of the present invention.

In the present invention, a $Tm^0$ is a temperature at which the anti-target nucleic acid molecule and the oligo nucleic acid molecule of 50% of the total molecular beacon are separated from each other.

The Tm0 value of the molecular beacon may be greater than 36° C., preferably greater than 50° C. When the Tm0 value is greater than 36° C., separation of the molecular beacon before reacting with a target material may be prevented and thus the probe may have enhanced stability, and in view of this, the Tm0 value is meaningful.

In addition, when the molecular beacon comes into contact with a target, a Tm value ($Tm^1$: a temperature at which, when the target-specific binding site of the anti-target nucleic acid molecule is bound to the target, 50% of the total target-specific binding site is separated from the target) of a target-binding site (target-specific binding site) may be lower than the $Tm^0$ value. In this case, since fluorescence can be exhibited only when the molecular beacon of the present disclosure is securely in contact with the target, detection accuracy may be enhanced.

In addition, when the molecular beacon is in contact with the target, a Tm value ($Tm^2$: a temperature at which, when the target-specific binding site of the anti-target nucleic acid molecule is bound to the target, the non-target site of 50% of the total anti-target nucleic acid molecule and the non-target site of the oligo nucleic acid molecule are separated from each other) of the non-target site, which does not bind to the target, may be lower than the $Tm^0$ value. The $Tm^2$ value may be lower than a reaction temperature. In this case, due to a reaction between the target and the probe, separation of the oligo nucleic acid molecule satisfactorily occurs and thus the probe of the present disclosure that has been in a quenching state due to the metal particles exhibits fluorescence, and thus the probe of the present disclosure may exhibit enhanced sensitivity.

In one embodiment of the present disclosure, target detectability of the probe was examined using three types of molecular beacons comprising anti-target nucleic acid molecules and oligo nucleic acid molecules, which satisfied the above conditions, and as illustrated in FIG. 5, it was experimentally confirmed that the detection of a target material is possible even at a very low amount, i.e., 1 pmole. Thus, the molecular beacons which satisfy the above conditions have high binding efficiency to the target and exhibit a fluorescence phenomenon through separation of the oligo nucleic acid molecule only when being completely in contact with the target, and thus a reduction in sensitivity due to a non-specific reaction may be prevented.

In one embodiment, the anti-target nucleic acid molecule may comprise guanine (G) in the non-target site. In particular, when the G sequence is comprised on an end side of the anti-target nucleic acid molecule to which the metal particles bind, quenching efficiency due to the metal particles may be further enhanced by a quenching effect due to the G base sequence. In this case, when the oligo nucleic acid molecule is separated from the molecular beacon by the target, a luminescence difference increases, and thus a detection signal becomes more distinct, and accordingly, diagnostic and therapeutic efficiency due to virus detection may be further enhanced.

In one embodiment, the anti-target nucleic acid molecule may further comprise a sequence of adenosine and thymine in the non-target site. The anti-target nucleic acid molecule, which is designed such that the sequence of adenosine and thymine is further comprised, may be more easily and rapidly separated from the oligo nucleic acid molecule when being in contact with a virus or a fragment thereof, and thus diagnostic and therapeutic effects of the probe may be enhanced.

As used herein, the term "metal particles" refers to particles consisting of a metal material, and in particular, the metal particles may be one or more selected from the group consisting of gold (Au), silver (Ag), platinum (Pt), and palladium (Pd), but the present disclosure is not limited thereto. The metal particles may be any metal particles with a size of 1 nm to 500 nm, preferably 20 nm to 200 nm.

The metal particles may be gold. In a case in which the probe of the present disclosure comprises a molecular beacon bound to gold, the probe has excellent quenching efficiency without binding a separate quencher thereto, in a state in which the anti-target nucleic acid molecule and the oligo nucleic acid molecule are bound to each other.

According to one embodiment of the present disclosure, as a result of examining the quenching efficiency of a prepared molecular beacon bound to gold, it was confirmed that the quenching efficiency of the molecular beacon was 80% or more without affecting absorption properties of the gold particles themselves.

The probe of the present disclosure may detect whether or not a virus is present in a sample or a cell, and thus may diagnose whether or not cells are infected with a virus or the presence or absence of a virus in a sample.

Therefore, in this aspect, the present disclosure provides a composition for detecting a virus, which comprises: metal particles; and a molecular beacon comprising an anti-target nucleic acid molecule and an oligo nucleic acid molecule.

The anti-target nucleic acid molecule of the probe may bind to surfaces of the metal particles and comprise a target-specific binding site, the oligo nucleic acid molecule may comprise an anti-target nucleic acid molecule-complementary binding site and a fluorescent material, and one or more molecular beacons may be bound to the metal particles.

The composition of the present disclosure may further comprise a buffer solution for detecting virus detection and an additional component such as a saline solution or the like, and the component may be any additional component that may be commonly used in the art.

Description of the metal particles and the molecular beacon is the same as described above.

The composition for detecting a virus may comprise two or more different type of probes. In addition, the probe may comprise two or more different types of molecular beacons.

When a subject is infected with various types of viruses, it is possible to diagnose and treat various types of viruses by using the composition comprising various types of probes or a probe comprising various types of molecular beacons. In particular, when a virus is present, a fluorescence signal is emitted when the oligo nucleic acid molecule is separated from the molecular beacon, and thus when this is measured, it is possible to diagnose the presence or absence of a viral infection in a sample or in a cell, and when a probe comprising two or more molecular beacons is used, wavelength bands of the fluorescent materials comprised in the respective molecular beacons are different from each other, and thus it is possible to detect the target by using the probe without interference phenomena due to the fluorescent materials.

In the case of an influenza virus, rapid diagnosis is required due to a fast transmission rate thereof, and, in the present disclosure, it is possible for the probe to perform rapid diagnosis on various subtypes of the influenza virus. In addition, the anti-target nucleic acid molecule directly binds to a virus, thereby inhibiting the proliferation of the virus, and thus the probe of the present disclosure may be effectively used as a therapeutic agent for a viral infection.

In one embodiment of the present disclosure, it was confirmed that, when treated with the probe of the present disclosure, the proliferation of a virus in cells was inhibited, and a smaller amount of the virus remained than in the case of being not treated with the probe, from which it was confirmed that the probe of the present disclosure simultaneously had detection and therapeutic effects.

In this aspect, the present disclosure relates to a composition for treating a viral infection, which comprises: metal particles; and a molecular beacon comprising an anti-target nucleic acid molecule and an oligo nucleic acid molecule.

The anti-target nucleic acid molecule of the probe may bind to surfaces of the metal particles and comprise a target-specific binding site, the oligo nucleic acid molecule may comprise a non-target site, an anti-target nucleic acid molecule-complementary binding site and a fluorescent material, and one or more molecular beacons may be bound to the metal particles.

The composition may be a pharmaceutical composition for treating a viral infection. The composition may comprise two or more different types of probes. In another embodiment, the composition may comprise a probe comprising two or more different types of molecular beacons. In this case, the composition is advantageous in that the anti-target nucleic acid molecule of each molecular beacon binds to the genetic material of each of two or more viruses, thereby having therapeutic effects on the viruses at the same time.

The composition may further comprise a pharmaceutically acceptable carrier. The pharmaceutically acceptable carrier comprises carriers and vehicles commonly used in the medical field, and examples thereof comprise, but are not limited to, ion exchange resins, alumina, aluminum stearate, lecithin, serum proteins (e.g., human serum albumin), buffer substances (e.g., various types of phosphates, glycine, sorbic acid, potassium sorbate, and partial glyceride mixtures of saturated vegetable fatty acids), water, salts or electrolytes (e.g., protamine sulfate, disodium hydrogen phosphate, potassium hydrogen phosphate, sodium chloride, and zinc salts), colloidal silica, magnesium trisilicate, polyvinyl pyrrolidone, cellulose-based substrates, polyethylene glycol, sodium carboxymethylcellulose, polyarylates, waxes, and lanolin.

In addition, the composition may further comprise, in addition to the above-described components, a lubricant, a wetting agent, an emulsifying agent, a suspending agent, a preservative, or the like. The composition for detecting a virus or treating a viral infection may be prepared as an aqueous solution for parenteral administration, and preferably a buffer solution such as a Hank's solution, a Ringer's solution, or a physically buffered saline may be used. An aqueous injection suspension may comprise a substrate capable of increasing the viscosity of the suspension, such as sodium carboxymethylcellulose, sorbitol, or dextran.

The probe of the present disclosure inhibits the proliferation of a virus when the anti-target nucleic acid molecule bound to the surfaces of the metal particles binds to the virus due to a miRNA sponge effect, thereby having an effect of treating a viral infection.

In addition, the present disclosure relates to a method of detecting a virus, comprising: treating a sample obtained from a subject with the above-described probe; and measuring a fluorescence change of the sample treated with the probe.

When the probe or the composition for detecting a virus, which comprises the probe, is used, detection factors simultaneously targeting two or more viruses may be processed at one time, and thus an effect of simultaneously detecting various types of viruses with a small amount of sample is obtained. In particular, wavelength bands of fluorescent materials of the respective probes are different, and thus it is possible to detect various types of viruses without interference phenomena, and accordingly, diagnosis time may be shortened.

Hereinafter, the present disclosure will be described in further detail with reference to the following preparation examples and experimental examples. These examples are provided for illustrative purposes only and are not intended to limit the scope of the present disclosure.

EXAMPLES

Preparation Examples

Preparation Example 1: Synthesis of Gold Nanoparticles 140 mg of sodium citrate was dissolved in 100 ml of distilled water, the resulting solution was heated up to 100° C., and then 50 ml of a 1 mM HAuCl$_4$ solution was added thereto. The mixed solution was stirred for 15 minutes until the mixed solution turned into a black red color from a yellow color, thereby completing the synthesis of gold nanoparticles having a diameter of about 15 nm.

The synthesized gold nanoparticles were used in preparing a probe as described below.

Preparation Example 2: Design and Preparation of Beacon

In a conserved base sequence region among the RNA sequences of influenza viruses H1N1, H3N2, and H9N2, a stem region was selected as a target region. An anti-target nucleic acid molecule capable of complementarily binding to a target sequence, and an oligo nucleic acid molecule, which was shorter than the anti-target nucleic acid molecule, could complementarily bind thereto, and had an end to which a fluorescent material was bound, were designed.

A thiol group was attached to an end of the anti-target nucleic acid molecule to allow binding to metal particles. For the design of beacons, specific target sequence sites are shown in Table 1 below. Nucleic acid sequences of molecular beacons for these are shown in Table 2 below.

TABLE 1

| SEQ ID NO. | Virus | HA stem region sequence |
|---|---|---|
| 1 | H1N1 | 5'-TCT ATT CAA TCT AGA GGC CTA TTT-3' 3'-AGA TAA GTT AGA TCT CCG GAT AAA-5' |

TABLE 1-continued

| SEQ ID NO. | Virus | HA stem region sequence |
|---|---|---|
| 2 | H3N2 | 5'-AGA GGC AAA CCA GAG GCC TGT TC-3'<br>3'-TCT CCG TTT GGT CTC CGG ACA AG-5' |
| 3 | H9N2 | 5'-GCT GCA TCA GGT AGA GGG CTA TTT-3'<br>3'-CGA CGT AGT CCA TCT CCC GAT AAA-5' |

TABLE 2

| Target | Molecular beacon structure | | Tm° (□) | ΔG (kcal/mol) |
|---|---|---|---|---|
| H1N1 | SEQ ID NO: 24-Anti-target | 5'-GGGGGCAC TTTTAGGCCTC TAGATTGAATA GA-3' | 61.09 | −19.53 |
| | SEQ ID NO: 25-Oligo | FAM-CCCGTGA AAATCCGGAGA | | |
| H3N2 | SEQ ID NO: 26-Anti-target | 5'-GGGGGCAC TTTACAGGCCT CTGGTTTGCCT CT-3' | 61.32 | −20.19 |
| | SEQ ID NO: 27-Oligo | ROX-CCCGTGA AATGTCCGGAG | | |
| H9N2 | SEQ ID NO: 28-Anti-target | 5'-GGGGGCAC TTTTAGCCCTC TACCTGATGCA GC-3' | 61.09 | −19.53 |
| | SEQ ID NO: 29-Oligo | Cy5-CCCGTGA AAATCGGAGA | | |

As shown in Table 2, the anti-target nucleic acid molecule and the oligo nucleic acid molecule were designed such that when the two molecules were bound to each other, the Tm value (Tm°) became 50° C. or more. Lastly, different fluorescent materials (FAM, ROX, and Cy5) were bound to the oligo nucleic acid molecule such that fluorescence wavelength bands of the three molecular beacons did not overlap with one another.

In addition, as shown in Table 3 below, molecular beacons for the virus H1N1 were prepared by varying the sequence of a non-target site, and properties thereof were identified.

TABLE 3

| Type | SEQ ID NO. | Nucleic acid sequence | Tm° (□) | GC % | Tm¹ (□) | Tm² (□) |
|---|---|---|---|---|---|---|
| Anti-target | SEQ ID NO: 10 | 5'-GGGGGAAATT TTAGGCCTCTAGA TTGAATAGA-3' | 55.61 | 50 | 54.78 | 20.62 |
| Oligo | SEQ ID NO: 11 | FAM-CCCTTTAAA ATCCGGAGA | | | | |
| Anti-target | SEQ ID NO: 12 | 5'-GGGGGCAATT TTAGGCCTCTAGA TTGAATAGA-3' | 58.87 | 55 | 54.78 | 27.08 |
| Oligo | SEQ ID NO: 13 | FAM-CCCGTTAAA ATCCGGAGA | | | | |
| Anti-target | SEQ ID NO: 14 | 5'-GGGGGCCATT TTAGGCCTCTAGA TTGAATAGA-3' | 61.09 | 60 | 54.78 | 31.2 |
| Oligo | SEQ ID NO: 15 | FAM-CCCGGTAAA ATCCGGAGA | | | | |
| Anti-target | SEQ ID NO: 16 | 5'-GGGGGCCCTT TTAGGCCTCTAGA TTGAATAGA-3' | 63.58 | 65 | 54.78 | 35.29 |
| Oligo | SEQ ID NO: 17 | FAM-CCCGGGAAA ATCCGGAGA | | | | |
| Anti-target | SEQ ID NO: 18 | 5'-GGGGGCCCGT TTAGGCCTCTAGA TTGAATAGA-3' | 66.38 | 70 | 54.78 | 41.27 |
| Oligo | SEQ ID NO: 19 | FAM-CCCGGGCAA ATCCGGAGA | | | | |
| Anti-target | SEQ ID NO: 20 | 5'-GGGGGCCCGG TTAGGCCTCTAGA TTGAATAGA-3' | 68.82 | 75 | 54.78 | 45.57 |
| Oligo | SEQ ID NO: 21 | FAM-CCCGGGCCA ATCCGGAGA | | | | |
| Anti-target | SEQ ID NO: 22 | 5'-GGGGGCCCGG GTAGGCCTCTAGA TTGAATAGA-3' | 71.28 | 80 | 54.78 | 47.68 |
| Oligo | SEQ ID NO: 23 | FAM-CCCGGGCCC ATCCGGAGA | | | | |

TABLE 3-continued

| Type | SEQ ID NO. | Nucleic acid sequence | Tm° (□) | GC % | Tm$^1$ (□) | Tm$^2$ (□) |
|---|---|---|---|---|---|---|
| Anti-target | SEQ ID NO: 30 | 5'-TTTTTAAATT TTAGGCCTCTAGA TTGAATAGA-3' | 48.79 | 25 | 54.78 | 5.45 |
| Oligo | SEQ ID NO: 31 | FAM-AAATTTAAA ATCCGGAGA | | | | |
| Anti-target | SEQ ID NO: 32 | 5'-GTTTTAAATT TTAGGCCTCTAGA TTGAATAGA-3' | 48.79 | 30 | 54.78 | 5.45 |
| Oligo | SEQ ID NO: 33 | FAM-AAATTTAAA ATCCGGAGA | | | | |
| Anti-target | SEQ ID NO: 34 | 5'-GGTTTAAATT TTAGGCCTCTAGA TTGAATAGA-3' | 46.86 | 35 | 54.78 | 4.52 |
| Oligo | SEQ ID NO: 35 | FAM-AAATTTAAA ATCCGGAGA | | | | |
| Anti-target | SEQ ID NO: 36 | 5'-GGGTTAAATT TTAGGCCTCTAGA TTGAATAGA-3' | 50.37 | 40 | 54.78 | 11.52 |
| Oligo | SEQ ID NO: 37 | FAM-CAATTTAAA ATCCGGAGA | | | | |
| Anti-target | SEQ ID NO: 38 | 5'-GGGGTAAATT TTAGGCCTCTAGA TTGAATAGA-3' | 52.67 | 45 | 54.78 | 15.4 |
| Oligo | SEQ ID NO: 39 | FAM-CCATTTAAA ATCCGGAGA | | | | |

Tm$^1$: A Tm value (□) at which, when the molecular beacon was in contact with the target, both a target-specific binding site (expressed as bold) and an anti-target nucleic acid molecule-complementary binding site (expressed as bold) were bound to the target
Tm$^2$: A Tm value (□) of a non-target site to which the target did not bind when the molecular beacon was in contact with the target (a Tm value of a portion not expressed as bold)

In a case in which, when the Tm° value was more than 36° C., the following condition: Tm°>Tm$^1$ was satisfied, and the Tm$^2$ value was lower than the Tm° value, it was confirmed that a binding strength between the target and the molecular beacon and a detection effect thereof were excellent, and a reduction in sensitivity due to a non-specific reaction was not observed. Thus, it was confirmed that, when a ratio of C/G in the non-target site was 50% or more, detection by the molecular beacon and therapeutic efficiency thereof could be enhanced.

Preparation Example 3: Preparation of Probe Comprising Gold-Beacon 125 pmoles of a beacon was allowed to bind to 0.25 pmole of the gold nanoparticles prepared according to Preparation Example 1. At this time, the three beacons prepared according to Preparation Example 2, shown in Table 2, at a total amount of 125 pmoles, were allowed to react with the gold nanoparticles.

Binding between the gold nanoparticles and the molecular beacons was performed using a salt aging method, which is a method of increasing the number of beacons bound to a surface of gold by gradually increasing the concentration of a salt. In particular, the salt aging method was performed by adding, every 20 minutes, 0.01% of sodium dodecyl sulfate (SDS), 0.01 M phosphate buffer (PB), and 2M sodium chloride (NaCl) to the 0.01% SDS/0.01 M PB dibasic solution comprising 0.25 pmole of gold nanoparticles and 125 moles of beacons until a final concentration of NaCl reached 1 M (specific volumes added are the same as shown in Table 4 below). By this method, agglomeration of the beacons was prevented and a greater number of beacons were bound to surfaces of the gold nanoparticles, thereby completing the preparation of a probe.

TABLE 4

| | Concentration (M) | | | | | | | | | | | | |
|---|---|---|---|---|---|---|---|---|---|---|---|---|---|
| | 0 | 0.05 | 0.1 | 0.2 | 0.3 | 0.4 | 0.5 | 0.6 | 0.7 | 0.8 | 0.9 | 1.0 |
| NaCl Buffer (λ) | 0 | 12.5 | 13.15 | 28.52 | 31.85 | 35.86 | 40.63 | 46.43 | 53.57 | 62.5 | 7.86 | 88.64 |

[Experimental Example 1] Identification of Properties of Probe

Experimental Example 1-1. Identification of Morphological and Physical Properties of Probe Morphological and physical properties of a complex of the gold nanoparticles synthesized according to Preparation Example 1 and the beacons shown in Table 2, i.e., the prepared probe (gold-beacon), were examined to analyze properties of the probe (Preparation Example 3).

In particular, the morphology of the probe was examined using an electron microscope (transmission electron microscopy, TEM), a zeta potential of the probe was measured to identify surface charge properties, and an average particle diameter of the probe was measured using a nanoparticle analyzer (dynamic light scattering, DLS). In addition, UV absorbance and fluorescence quenching efficiency of each of the gold nanoparticles and the probe were measured to identify binding properties.

As illustrated in FIGS. 1A, 1B, 1C, and 1D, it was confirmed that the probe in which the molecular beacons were bound to the gold nanoparticles had a larger size and a lower surface charge, than those in the case of nanoparticles to which a beacon was not bound. In addition, it was confirmed that, although the molecular beacons were bound to the gold nanoparticles, their intrinsic absorbance properties were unchanged, and quenching efficiency of the molecular beacons was 80% or more.

Experimental Example 2-1. Measurement of Fluorescence Signal of Probe

It was examined whether a fluorescence signal was satisfactorily emitted when the probe of Preparation Example 3 was in contact with a target virus sequence. 4 mN of the gold nanoparticles-beacons complex and 4 pmoles of nucleotides of a target sequence of each of the viruses H1N1, H3N2, and H9N2 were incubated, and then a change in the intensity of a fluorescence signal of the probe according to the presence or absence of the target sequence was examined. Results thereof are illustrated in FIGS. 2A, 2B, and 2C.

As illustrated in FIGS. 2A, 2B, and 2C, it was confirmed that fluorescence was detected for all the three virus subtypes only in the presence of the target sequence, from which it was confirmed that the probe of the present disclosure was capable of specifically detecting all the subtypes of each virus.

[Experimental Example 2] Identification of Virus Detection Effect Using Probe

It was examined whether the probe of the present disclosure was capable of treating virus-infected cells through a miRNA sponge effect.

Cells were put in a 96-well plate at a density of $1 \times 10^4$ cells/well, and stabilized for 24 hours. The cells were treated with the virus H1N1 at a concentration of $10^7$ TCID, followed by culturing for 12 hours, to infect the cells with the virus. Thereafter, 6.3 uM of the probe was incubated along with the cells for 1 hour. In addition, the cells were incubated in the same manner as described above at concentrations at which the initial concentration of the probe was diluted by ½ each time. Then, a fluorescence signal emitted by the oligo nucleic acid molecule due to binding of the virus to the anti-target nucleic acid molecule was measured.

As a result, as illustrated in FIGS. 3A and 3B, it was confirmed that, when H1N1-infected cells were treated with the probe in which the molecular beacon complementary to H1N1 was bound, in the H1N1-infected cells treated with the probe at a concentration diluted up to $\frac{1}{16}$, the probe emitted a fluorescence signal by recognizing a H1N1 influenza sequence, and the viability of the cells was increased at the same concentration. Thus, it was confirmed that it was possible to simultaneously detect and treat a virus by using the probe of the present disclosure.

[Experimental Example 3] Verification of Effect of Probe on Detecting and Inhibiting Proliferation of Virus in Cells After measuring the fluorescence signal in Experimental Example 2, the supernatant of the cells was collected, followed by a hemagglutination (HA) assay.

Supernatants of the cells treated with the probe at various concentrations (diluted to $\frac{1}{2}^n$ each time from ½ to 1/4096) were diluted and a dilution factor at which coagulation occurred when red blood cells were added thereto was investigated.

As illustrated in FIGS. 4A and 4B, it can be confirmed through titer values that in the case of treatment with the probe of the present disclosure, the proliferation of the virus is inhibited, and thus a smaller number of viruses remains than that of a positive control (P.C). Thus, it was confirmed that in the case of treatment with the probe of the present disclosure, the proliferation of the virus was inhibited by binding of the probe, and thus it was possible to simultaneously perform diagnosis and treatment according to virus detection.

[Experimental Example 4] Identification of Detectability of Probe According to Concentration of Target The detectability of the probe of the present disclosure according to the concentration of a target sequence was examined using the probe (AuMB) consisting of the gold particles-molecular beacons complex, prepared according to Preparation Example 3. AuMB (at this time, the amount of the molecular beacons comprised in AuMB was 10 pmoles) in which the three beacons shown in Table 2 (beacons for H1N1, H3N2, and H9N2) were attached was added to a sample comprising 1 pmole, 2 pmoles, 4 pmoles, 8 pmoles, or 16 pmoles of a nucleic acid molecule of a target sequence (H1N1 sequence); a nucleic acid molecule of a non-target sequence (scramble sequence; 5'-GTA CTT ATT AGG CGG-3', SEQ ID NO: 40); or a nucleic acid molecule of a mixture thereof (the target sequence and the non-target sequence at a molar ratio of 1:1), and was allowed to react at 37° C. for 2 hours, and then fluorescence of the probe was measured.

As a result, as illustrated in FIG. 5, it was confirmed that the fluorescence signal of the probe was increased only in the case of the target sequence, and even in a case in which the target sequence was present in the sample at an amount of 1 pmole, a difference in fluorescence signal was exhibited, and thus it was possible to detect even a very low amount of virus by using the probe of the present disclosure.

As is apparent from the foregoing description, a probe of the present disclosure can simultaneously perform diagnosis by virus detection and treatment of virus-infected cells. In particular, the probe of the present disclosure can simultaneously perform diagnosis and treatment on various types of viruses by varying the type of molecular beacon, and thus can be usefully applied to virus diagnosis and treatment fields, which require rapid diagnosis and treatment, and can effectively prevent the spread of infection. In addition, the probe of the present disclosure has excellent stability and excellent detection sensitivity, and thus it is possible to detect a very low amount of target at the picomole (pmole) level.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A probe for detecting and/or treating a virus, the probe comprising:

a metal particle; and one or more molecular beacons, each molecular beacon comprising an anti-target nucleic acid molecule and an oligo nucleic acid molecule, wherein the anti-target nucleic acid molecule is bound to the surface of the metal particle and comprises a non-target site and a target-specific binding site;

wherein the oligo nucleic acid molecule comprises a non-target site, an anti-target nucleic acid molecule-complementary binding site and a fluorescent material;

wherein the GC content in the non-target site of the anti-target nucleic acid molecule is 50% or more and the GC content in the non-target site of the oligo nucleic acid molecule is 50% or more;

wherein the non-target site of the oligo nucleic acid molecule complementarily binds to the non-target site of the anti-target nucleic acid molecule;

wherein the anti-target nucleic acid molecule and the oligo nucleic acid molecule are two separate nucleic acid strands, wherein the probe has a temperature ($Tm^0$) greater than or equal to 36° C. ($Tm^0 \geq 36°$ C.), the temperature ($Tm^0$) being a temperature at which for a population of identical molecular beacons, the anti-target nucleic acid molecule and the oligo nucleic acid molecule of 50% of the total molecular beacons are separated from each other;

wherein the probe has a temperature ($Tm^1$) that is lower than $Tm^0$ ($Tm^0 > Tm^1$), the temperature ($Tm^1$) being a temperature at which for a population of identical molecular beacons, when the target-specific binding site of the anti-target nucleic acid molecule is bound to a target, 50% of the total target-specific binding site is separated from the target; and wherein the probe has a temperature ($Tm^2$) that is lower than $Tm^0$ and $Tm^1$, the temperature ($Tm^2$) being a temperature at which for a population of identical molecular beacons, when the target-specific binding site of the anti-target nucleic acid molecule is bound to a target, 50% of a non-target site of the anti-target nucleic acid molecule is separated from a non-target site of the oligo nucleic acid molecule.

2. The probe of claim 1, wherein the probe comprises two or more molecular beacons of two or more types, wherein the target of each of the anti-target nucleic acid molecules in the two or more molecular beacons are different from each other, and the fluorescent material of each of the oligo nucleic acid molecules in the two or more molecular beacons has a different emission wavelength.

3. The probe of claim 1, wherein the target-specific binding site of the anti-target nucleic acid molecule complementarily binds to a nucleic acid sequence encoding a stem region in a hemagglutinin (HA) protein of an influenza virus.

4. The probe of claim 3, wherein the virus comprises one or more selected from the group consisting of H1N1, H2N2, H3N2, H5N1, H7N7, and H9N2.

5. The probe of claim 1, wherein the anti-target nucleic acid molecule comprises a non-target site and a target-specific binding site having a sequence of 2 to 24 nucleotides, the sequence complementarily binds to any one nucleic acid sequence selected from the group consisting of SEQ ID NOS: 1 to 3.

6. The probe of claim 1, wherein the metal is one or more selected from the group consisting of gold (Au), silver (Ag), platinum (Pt), and palladium (Pd).

7. The probe of claim 1, wherein the fluorescent material is one or more selected from the group consisting of rhodamine or derivatives thereof, fluorescein or derivatives thereof, coumarin or derivatives thereof, acridine and derivatives thereof, pyrene and derivatives thereof, erythrosine and derivatives thereof, eosin or derivatives thereof, cyanine or derivatives thereof, and 4-acetamido-4'-isothiocyanatostilbene-2,2'-disulfonic acid.

8. The probe of claim 1, wherein the virus is an influenza virus.

9. A composition for detecting a virus comprising the probe according to claim 1, wherein the composition comprises two or more different types of probes that detect different targets.

10. A method of treating a viral infection, the method comprising:
    administering to a virus-infected subject the probe according to claim 1.

11. The method of claim 10, wherein the probe comprises two or more molecular beacons.

12. A method of detecting a virus, the method comprising:
    contacting a sample obtained from a subject with the probe according to claim 1; and
    measuring a change in fluorescence of the sample contacted with the probe.

* * * * *